United States Patent [19]
Omar

[11] Patent Number: 6,086,884
[45] Date of Patent: *Jul. 11, 2000

[54] COMPOSITION FOR TREATING IMPOTENCE IN MEN CONTAINING DRIED ROE AND YOHIMBINE

[76] Inventor: Lotfi Ismail Omar, P.O. Box F396, Kew Gardens, N.Y. 11415

[*] Notice: This patent is subject to a terminal disclaimer.

[21] Appl. No.: 09/023,652

[22] Filed: Feb. 7, 1998

Related U.S. Application Data

[63] Continuation-in-part of application No. 08/660,875, Jun. 6, 1996.

[51] Int. Cl.⁷ .................................................. A61K 35/78
[52] U.S. Cl. ........................ 424/195.1; 424/561; 424/451; 424/641; 424/682; 424/702; 514/78
[58] Field of Search .................................. 424/195.1, 561, 424/451, 641, 682, 702; 514/78

[56] References Cited

U.S. PATENT DOCUMENTS 5,730,987  3/1998  Omar ................................. 424/195.1

*Primary Examiner*—Jean C. Witz
*Attorney, Agent, or Firm*—Michael I. Kroll

[57] ABSTRACT

A composition for treating impotence in human males contains a synergistic mixture of dried sturgeon roe and yohimbine hydrochloride wherein the weight percent ratio of said dried sturgeon roe:yohimbine hydrochloride is from about 25:1 to 1000:1, with an optimum ratio of about 132:1. The roe can be dried via either lyophilization or air drying under ambient temperature and pressure with reduced environmental humidity. A method of treating impotence in human males includes administration of such compositions containing the synergistic mixture of roe and yohimbine. Also, a method of treating impotence in human males by administration of dried roe in doses of from 300 to 900 mg. The roe is prepared either via lyophilization or air drying under ambient temperature and pressure with reduced environmental humidity.

22 Claims, 2 Drawing Sheets

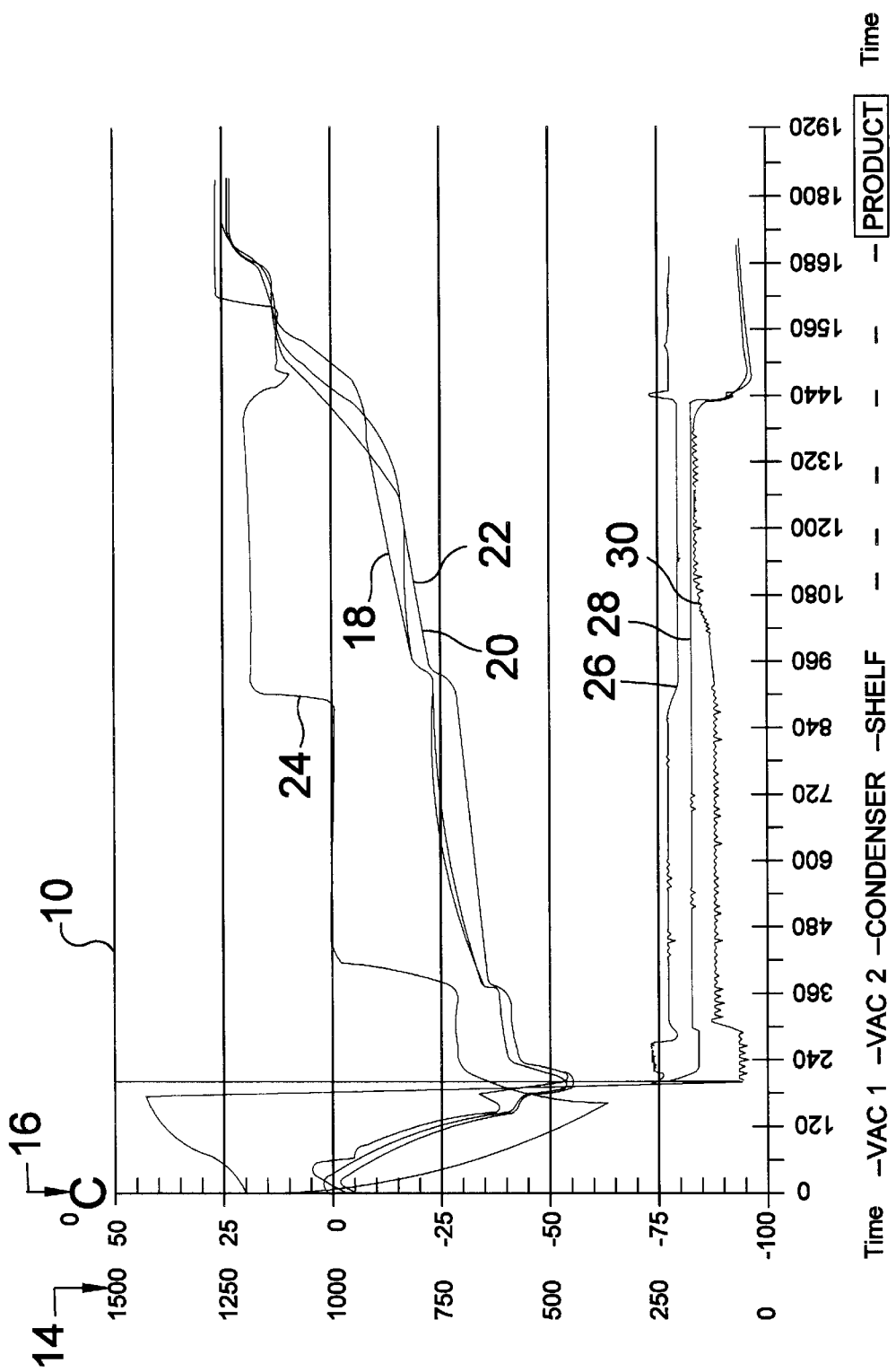

34 {
Name_____ Color Code_____
Age_____
Job_____
Health Condition  ☐Poor  ☐Average  ☐Good
Telephone & Address_____

Date Started Treatment:_____
Marital Status     ☐Married  ☐Single
Other Medications Taken:_____

☐Diabetic  ☐High B. P.  ☐Heart Cond.  ☐Cholesterol

|  | Column #1 | Column #2 | Column #3 | Column #4 |
|---|---|---|---|---|
| Function | Before Using | After 4 weeks | After 8 weeks | Ater 12 weeks |
| Sexual or Libido | strong ☐<br>fair ☐<br>weak ☐ | strong ☐<br>fair ☐<br>weak ☐ | strong ☐<br>fair ☐<br>weak ☐ | strong ☐<br>fair ☐<br>weak ☐ |
| Description of Erection | hard ☐<br>semi-hard ☐<br>no erection ☐ | hard ☐<br>semi-hard ☐<br>no erection ☐ | hard ☐<br>semi-hard ☐<br>no erection ☐ | hard ☐<br>semi-hard ☐<br>no erection ☐ |
| Frequency of Intercourse per month | 4 or more ☐<br>3 ☐<br>2 ☐<br>1 ☐<br>0 ☐ | 4 or more ☐<br>3 ☐<br>2 ☐<br>1 ☐<br>0 ☐ | 4 or more ☐<br>3 ☐<br>2 ☐<br>1 ☐<br>0 ☐ | 4 or more ☐<br>3 ☐<br>2 ☐<br>1 ☐<br>0 ☐ |

FIG 2

COMPOSITION FOR TREATING IMPOTENCE IN MEN CONTAINING DRIED ROE AND YOHIMBINE

CROSS-REFERENCE TO RELATED APPLICATION

This application is a continuation-in-part of my application Ser. No. 08/660,875, filed Jun. 6, 1996, entitled "Medication for Impotence Containing Lyophilized Roe and a Powdered Extract of Ginkgo Biloba," currently pending, which is incorporated herein by this reference.

BACKGROUND OF THE INVENTION

1. Field of the Invention

The instant invention relates generally to a composition for treating impotence in men that relieves erectile dysfunction and enhances sexual desire, and specifically to a composition for treating impotence by using fish roe either alone or in combination with yohimbine. The invention relates also to methods of preparing fish roe for use as a pharmaceutical product to treat impotence and for incorporation into the compositions of the present invention.

2. Description of the Prior Art

Therapies for treating impotence are known in the art. These include the compositions and treatment methods described below.

Hormonal Treatments (Androgens)

Testosterone and its derivatives are obtained only by prescription. They are administered orally or via injection, buccal tablets or other pharmaceutical dosage forms. The main use is for hypogonadism, male climactric and impotence. Testosterone also has other applications in medicine. As with other hormonal treatments, during administration of exogenous testosterone, endogenous testosterone release is inhibited through the negative feedback mechanism of pituitary lutenizing hormone (LH, or lutropin).

Large doses of exogenous androgens may suppress spermatogenesis through a negative feedback response by inhibition of pituitary follicle stimulating hormone (FSH, or follitropin). This characteristically results in inadequate endogenous testosterone production once exogenous testosterone administration is discontinued.

Testosterone and its derivatives have been used successfully to develop or to maintain sexual characteristics and other physiologic functions in androgen deficient males. However it is of no benefit to patients that are not androgen deficient as can be demonstrated by plasma testosterone levels.

Yohimbine

Yohimbine is an indolalkylamine alkaloid having the chemical formula $C_{21}H_{26}O_3N_2$ and a molecular weight of 354.5. It is the principal alkaloid of the bark (yohimbehe) of the west African *Corynanthe johimbe* (Rubiaceae) tree. Other, informal names for yohimbine include quebrachine, methyl yohimbate and corynine.

Yohimbine is primarily an $a_2$ adrenergic blocker, i.e., it blocks presynaptic $a_2$ adrenoreceptors causing release of norepinephrine. Its peripheral autonomic nervous system effect is to increase parasympathetic (cholinergic) activity and to decrease sympathetic (adrenergic) activity. In male sexual performance, erection is linked to cholinergic activity which theoretically results in increased penile blood inflow, decreased penile blood outflow, or both, causing erectile stimulation without increasing sexual desire (*Drug Facts and Comparison*, p. 731h, April 1995).

Yohimbine has been successfully used to treat impotence in some patients, particularly those with conditions of vascular or diabetic origin. A typical effective dosage of yohimbine in such treatments is 18 mg/day. At such dosages, yohimbine is known to produce various side effects, for example, increased blood pressure and heart rate, paresthesias and others. These side effects make such dosages unsuitable for patients with renal disease, cardio-renal disorders, gastric or duodenal ulcerations, and for psychiatric and geriatric patients.

Papaverine

Papaverine injection is only available by prescription; generally it is not the treatment of choice for impotence patients. Papaverine has been used as an injection administered into the penis directly. Erection usually occurs within 5–15 minutes after injection. Papaverine injection causes pain and bruising at the site of injection. Persistent painful erection that occurs independently of sexual desire (priapism) is a side effect which often lasts from 5–7 hours causing embarrassment and discomfort to the patient. Fibrous growth in the penis tissue has also been reported.

Caverject

Caverject is a brand name marketed and available only by prescription. It is the synthetic version of alprostadil (prostaglandin E) which the body uses to help produce an erection. The medication is injected directly into the penis shortly before intercourse. It relaxes smooth muscle tissue in the penis which in turn enhances blood flow to the penis and causes erection. Caverject is often effective for men whose impotence is due to diabetic complications, anxiety or radical prostatectomy. One of the major drawbacks of caverject is that the subject, after injection, may have long lasting painful erection (priapism), which may last more than 6 hours and cause serious and permanent damage to the delicate spongy structure of the penis which may never again function properly.

Penile Implants

Penile implants, primarily made from silicone rubber, are surgically inserted in the shaft of the penis to make it sufficiently rigid for vaginal intercourse. Penile implant operations were first preformed in the 1960's and now some 30,000 men have the surgery each year. Penile implants come in different styles and sizes; semirigid, flexible rods or cylinders that are surgically inserted into both sides of the penis but do not get as hard as a natural erection. Men with this kind of implant have permanent enlargement (erection).

Inflatable Implants

Inflatable implants are another type of penile implant. They consist of twin cylinders connected to a pump and a fluid-filled reservoir. The cylinders are inserted in the penis, the pump concealed in the scrotum and the reservoir in the abdominal cavity. When the pump is squeezed, the fluid is forced out of the reservoir into the cylinders, causing an erection. When the pump is squeezed again, the fluid is released back into the reservoir, lowering the erection.

Implants have their own drawbacks; they are uncomfortable, require surgery which may have serious complications, are very expensive, and not every man is a candidate for penile implantation. Most men look for less invasive remedies.

In addition to the treatments described above, the following substances are often misconceived as sex stimulants.

Marijuana

Some people think marijuana use will cause sexual stimulation, however marijuana is more likely to be a sexual depressant and is also illegal to possess or use in many states.

Alcohol

Alcohol is also perceived as a sexual stimulant but is actually a sexual depressant and results in liver damage when consumed in quantity.

Amyl Nitrate

Amyl nitrate has been used (as an inhalant) because of its peripheral vasodilation effect which is perceived as a sexual stimulant, but actually is not. Its side effects are of serious concern, particularly in men and women with hypertension or over the age of 40.

BRIEF SUMMARY OF THE INVENTION

It is, therefore, an object of the present invention to provide a composition for treating impotence which will achieve positive effects on both the libido and the penile erectile function, both of which are necessary for optimal sexual performance.

An additional object is to reinstate self-confidence in the patient by successfully treating his impotence.

It is also an object of the present invention to provide a composition to treat impotence that is safe, effective, and easy to administer with minimal or no side effects.

It is still a further object of the present invention to provide a composition for treating impotence that will overcome the shortcomings of the prior art through a more holistic approach that emphasizes the synergistic action of the two ingredients, lyophilized roe and yohimbine.

It is yet a further object of the invention to provide a product that has a synergistic effect that will dramatically improve the sexual activity of the man.

Another object is to provide a method for drying fresh roe for use in a composition for treating impotence by drying the roe either through lyophilization (freeze-drying) or by drying under ambient temperatures and pressures with reduced humidity; the dried roe can then be put into hard gelatin capsules for oral use to treat impotence or reduced sexuality in human male subjects, or the dried roe can be blended with yohimbine hydrochloride and that mixture packed in capsules for oral use.

Yet another object is to provide a composition for treating impotence which contains a synergistic combination of about 99 weight percent dried fish roe and about 1 weight percent yohimbine HCl.

A further object of the present invention is to provide a product composed of natural constituents that will serve the purpose of solving the dilemma of impotence without using harsh devices or causing any damage or serious side effects to the body.

A final object is to provide a composition for treating impotence that is economical in cost both to the manufacturer and to the patient.

The foregoing and other objects, advantages and characterizing features will become apparent from the following description of certain illustrative embodiments of the invention.

The novel features which are considered characteristic for the invention are set forth in the appended claims. The invention itself, however, both as to its construction and its method of operation, together with additional objects and advantages thereof, will be best understood from the following description of the specific embodiments when read and understood in connection with the accompanying drawings. Attention is called to the fact, however, that the drawings are illustrative only, and that changes may be made in the specific construction illustrated and described within the scope of the appended claims.

BRIEF DESCRIPTION OF THE DRAWING FIGURES

Various other objects, features and attendant advantages of the present invention will become more fully appreciated as the same becomes better understood when considered in conjunction with the accompanying drawings, in which like reference characters designate the same or similar parts throughout the several views.

FIG. 1 is a graphic representation of the lyophilization process of the present invention.

FIG. 2 is representative example of a self-assessment form for use by the patient to monitor his sexual activity before and during the treatment process.

DETAILED DESCRIPTION OF THE PREFERRED EMBODIMENTS

Turning now descriptively to the drawings, in which similar reference denote similar elements throughout the several views, the Figures illustrate the lyophilization process of the present invention. With regard to the reference numerals used, the following numbering is used throughout the various drawing figures.

10 lyophilization conditions graph
12 the x-axis of 10, denoting the time in minutes, of lyophilization
14 first y-axis of 10, denoting the pressure in millitorr, of lyophilization
16 second y-axis of 10, denoting the temperature in ° C., of lyophilization
18 first product sample temperature
20 second product sample temperature
22 third product sample temperature
24 shelf temperature
26 pressure measured at condenser
28 pressure measured at first vacuum pump
30 pressure measured at second vacuum pump
32 self-evaluation chart for patient
34 personal information portion of 32
36 sexual evaluation portion of 32
38 first portion of 36, evaluation of libido
40 second portion of 36, evaluation of erection
42 third portion of 36, evaluation of sexual frequency
44 first measurement of 36, prior to treatment
46 second measurement of 36, after 4 weeks of treatment
48 third measurement of 36, after 8 weeks of treatment
50 fourth measurement of 36, after 12 weeks of treatment
52 comments portion of 32

The present invention relates to a composition for treating impotence in human males comprising a mixture of dried roe and yohimbine. It has been unexpected found that the combination of roe and yohimbine, particularly sturgeon roe and yohimbine hydrochloride, acts synergistically in humans for improving sexual performance. The synergistic effect should be present for compositions wherein the weight percent ratio of roe:yohimbine is between 25:1 and 1000:1, more particularly between 50:1 to 500:1, with the greatest synergy between 0:1 and 200:1, with a particularly preferred composition being 132:1.

The composition can be administered orally in any suitable form, such as in a capsule, for example, a hard gelatin capsule. Such capsules generally contain between 300 and 900 mg of the composition, usually about 600 mg.

The composition can contain further pharmaceutically acceptable adjutants, for example, nutritional vitamins and/or minerals, herb and/or other plant extracts, preservatives, stabilizers, colorants, flavoring agents and the like.

With regard to the dried roe, it is preferred to use dried fresh sturgeon roe. While any methods of drying which do not destroy the various active components of the roe are appropriate, two particular methods are preferred. The first is lyophilization, or freeze-drying. The second is drying the roe at or near room temperature and pressure, but under reduced humidity with circulating air.

The lyophilization process of the present invention is effective in preparing dried lyophilized roe having a total moisture content under 5 weight percent from fresh roe having a moisture content of at least 30 weight percent, (most fresh roe contains from 37 to 79 weight percent water). The various steps include lyophilizing the roe by exposing it to a temperature of −20° C. or less and a pressure of 300 millitorr or less, preferably a temperature of −30° C. or less and a pressure of 200 millitorr or less are used until the total moisture content of the roe is less than 5 weight percent, preferably under 4 weight percent, grinding the lyophilized roe to a powder, and adding to the lyophilized roe powder one or more preservatives, such as, for example, methyl paraben, propyl paraben, BHA and BHT.

The second method of drying the roe utilizes room temperature and pressure conditions with reduced environmental humidity in conjunction with circulating air. This method is also suitable for preparing dried roe having a total moisture content under 5 weight percent from fresh roe and relies on the steps of spreading the roe in a thin, preferably between 3 and 10 mm, layer in a tray, placing the tray into a closed environment with temperature and humidity controls, maintaining the closed environment at about room temperature, for example, between 20 and 25° C., periodically mixing and respreading the roe in layers in the tray, circulating air within the closed environment over the roe layers, gradually decreasing the humidity of the environment by removing moisture from the air, preferably until the humidity is 55% or less, until the moisture content of the roe falls below 5 weight percent, removing the roe from the closed environment, grinding the roe to a powder; and adding to the roe powder one or more preservatives as described above.

Fish roe (commercially known as caviar) are the eggs of certain fish, most commonly sturgeon. It is prepared by removing the egg masses from freshly caught fish. Immediately after harvesting, salt is added, usually 4 to 6 weight percent, in order to preserve freshness and also to bring out the flavor. For further preservation, it is usually refrigerated and/or pasteurized. Most caviar is produced in Russia and Iran from fish taken from the Caspian and Black Seas and sold in U.S. and European markets. For centuries fish roe has played an important role in the diet of people around the world. For example, ancient civilizations in China and Egypt believed that consuming fish roe provided health benefits and preserved one's sexual potency.

Caviar is graded according to the size of the eggs and manner of processing, grades are named for the type of Sturgeon from which the eggs are taken. Beluga, the largest, is black or grey, the smaller, Osetrova, is grayish, grayish green or reddish brown. Caviar has been consumed as an appetizer for generations.

Caviar contains, by weight, approximately 36 to 79% moisture; 2.7 to 3.4% protein; 3 to 5% carbohydrates; 1.0 to 1.7% fats in the form of phospholipids, and 0.01 to 0.05% minerals. Approximately 32 elements can be detected in caviar, some of which include calcium, phosphorus, zinc, copper and iron. Certain vitamins are also detectable, such as vitamins A, E, riboflavin, niacin, $B_6$, calcium pantothenate and $B_{12}$. Of the fats, 70% of the whole lipids are unsaturated fatty acids. Most of these phospholipids occur either as phosphatidyl cholines (lecithins) or as phosphatidyl ethanolamine (cephalins), and to a lesser extent inositol phosphatides, cerebrosides and sphingomyelines.

Phospholipids play an essential role in message transmission between the nerve cells in our body. The phosphorus component helps keep nerve cells healthy, the phosphatidyl choline component assists in mental recuperation and helps increase mental activity.

In this study the dried fish roe was found to have a strong aphrodisiac effect on both men and women. It is believed that the roe has an effect on glands that control the secretion of sex hormones. Without the proper levels of sex hormones, a person tends to lose interest in sexual activity. It is believed that the connection between using the composition of the present invention and increased sexual activity is that the claimed composition may stimulate certain glands to secrete sex hormones. In all likelihood, the present invention stimulates the pituitary gland and other glands that control the secretion of sex hormones in both sexes.

The composition is blended using art recognized principles and methodologies in combining the ingredients together. A preferred embodiment of the present invention is prepared as follows.

Fresh roe (10.0 kg, 78.4 weight percent water content) obtained from Sturgeon species *Cyclopterus lumbus* was accurately weighed and placed into a freeze drying unit. As illustrated in FIG. 1, the fish roe was lyophilized at a starting temperature of −30° C. and a starting pressure of 200 millitorr. After 28 hours, 2.245 kg of dry roe are recovered, with a moisture content of about 3.7 weight percent. At completion of the drying process, the temperature was about 25° C. and the pressure was about 1250 millitorr. The dried roe was then ground into a fine powder and sieved through a fine mesh sieve.

The dried fine powdered fish roe thus obtained was then weighed and mixed with the following preservatives using geometric mixing according to well known methodology of the art to ensure the homogeneity and hygienity of the mixture: propyl paraben (0.1%); methyl paraben (0.2%); BHA (0.05%); and BHT (0.05%). The mixture thus produced is packed into hard gelatin capsules, each containing between 300 and 900 mg of the mixture, most commonly about 600 mg. The capsules are administered orally, 4 capsules per day, to a patient in need of such treatment for impotence. The regimen continues for 8 to 12 weeks or until a noticeable improvement in sexual activity is achieved.

Another method for obtaining dry powdered fish roe for use as a pharmaceutical product in treating impotence employs the following methodology.

Fresh sturgeon fish roe (10 kg) was evenly spread into ¼ inch (about 6.3 mm) thick layers placed onto liners set into trays. The trays were placed on racks kept in a closed room with a constant temperature range between 70 and 75° F. (about 20 to 25° C.), under atmospheric pressure, while a dehydrator was employed to remove moisture from the air. The trays were exposed to a steady flow of air from continuously running fans. After 24 hours the partially dried fish roe was mixed and respread into layers as before. The mixing and respreading process was repeated once every 24 hours, along with rotation of the trays in the racks, for a period of 5 days. During the first day of the process, the relative humidity was between 75 and 82%. Each day the humidity was reduced gradually by the action of the dehydrator until by the fifth day the relative humidity was between 42 and 47%. At this point the fish roe was dry enough for use in the instant composition. The dry fish roe granules were ground into a fine powder and sieved through a fine mesh sieve, and weighed, yielding 2.283 kg of roe, having a moisture content of about 4.8%.

The dried fine powdered fish roe thus obtained was then weighed and mixed with the following preservatives using geometric mixing according to well known methodology of the art to ensure the homogeneity and hygienity of the mixture: propyl paraben (0.1%); methyl paraben (0.2%); BHA (0.05%); and BHT (0.05%). The mixture thus produced is packed into hard gelatin capsules, each containing between 300 and 900 mg of the mixture, most commonly about 600 mg. The capsules are administered orally, 4 capsules per day, to a patient in need of such treatment for impotence. The regimen continues for 8 to 12 weeks or until a noticeable improvement in sexual activity is achieved.

In double-blind placebo-controlled studies, using the dried fish roe-containing capsules prepared and administered as described above, the dried fish roe was found to have a strong aphrodisiac effect on human male subjects. For treating impotence the patient is administered 2 of the dried fish roe capsules in the morning and 2 in the evening, preferably after meals to aid in absorption. Usually, a noticeable improvement will be achieved within 8 to 12 weeks of treatment; such improvement includes proper penile erection, enhanced libido and increased frequency of copulation, as measured by the chart illustrated in FIG. 2, which each patient instructed to assess these parameters before starting treatment and every 4 weeks during the treatment regimen.

The response to treatment depends on some factors such as the health condition of the patient before starting treatment, for example, blood sugar and cholesterol levels, age, duration of impotence prior to treatment, and any other medications which are taken concomitantly with the instant treatment. Those that may have negative side effects on sexual activity include, for example, some antidepressants and antihypertensives. The patient can stop taking the composition after reaching his goal in treating the impotence or he may continue taking it in order to continue to derive benefit therefrom, as the product is safe, all natural, and can be considered a dietary supplement.

Another method of treating impotence in a patient in need of such treatment involves the use of a mixture of dried fish roe and yohimbine, preferably yohimbine hydrochloride. It has been found that the roe and yohimbine act synergistically over a range of ratios (roe:yohimbine) of from 1000:1, more particularly between 50:1 to 500:1, with the greatest synergy between 100:1 and 200:1, and with a particularly preferred composition being 132:1. Expressed alternatively, a ratio of 132:1 produces a composition containing 99.25 weight percent roe and 0.75 weight percent yohimbine hydrochloride.

A preferred synergistic composition was prepared by the following methodology.

Dried sturgeon roe (595.5 g), prepared as described above, was mixed in a blender with yohimbine hydrochloride (4.5 g), using geometric mixing according to well known methodology of the art to ensure the homogeneity and hygienity of the mixture. The mixture consisted of the following ingredients on a weight percent basis:

| dry fish roe powder | 99.25% |
|---|---|
| yohimbine HCl Powder | 0.75% |

The blended mix is then packed into hard gelatin capsules, each containing 600 mg of the mixture, each capsule containing 595.5 mg fish roe powder and 4.5 mg yohimbine HCl powder. The dose for treating impotence is one capsule, taken orally three times daily, preferably after meals, for 6 to 8 weeks, or until improvement in sexual activity is achieved, but in any case for no longer than 10 weeks in order to avoid any complications from the adverse effects of the yohimbine contained in the formula. Most patients experience dramatic improvement in penile erection and in libido due to the synergistic effect of the mixture.

The fish roe increases the libido due to its stimulant effect on the glands that control sexual activity, while yohimbine relieves the erectile dysfunction due to its cholinergic effect on the penis. Both actions induce a dramatic effect on the sexual activity of the impotent patient.

It will be understood that each of the elements described above, or two or more together, may also find a useful application in other types of applications differing from the type described above.

While the invention has been illustrated and described as embodied in a composition for treating impotence, it is not intended to be limited to the details shown, since it will be understood that various omissions, modifications, substitutions and changes in the forms and details of the formulation illustrated and in its operation can be made by those skilled in the art without departing in any way from the spirit and scope of the present invention.

Without further analysis, the foregoing will so fully reveal the gist of the present invention that others can, by applying current knowledge, readily adapt it for various applications without omitting features that, from the standpoint of prior art, fairly constitute essential characteristics of this invention.

What is claimed and desired to be protected by Letters Patent is set forth in the appended claims:

1. A composition for treating impotence in human males comprising a mixture of dried Sturgeon roe and yohimbine wherein the weight percent ratio of said dried roe:yohimbine is from about 25:1 to 1000:1.

2. The composition for treating impotence in human males as defined in claim 1, wherein the weight percent ratio of dried Sturgeon roe:yohimbine is from about 50:1 to 500:1.

3. The composition for treating impotence in human males as defined in claim 1, wherein the weight percent ratio of dried Sturgeon roe:yohimbine is from about 100:1 to 200:1.

4. The composition for treating impotence in human males as defined in claim 2, wherein the weight percent ratio of dried Sturgeon roe:yohimbine is about 132:1.

5. The composition for treating impotence in human males as defined in claim 1, wherein said yohimbine is yohimbine hydrochloride.

6. The composition for treating impotence in human males as defined in claim 4, wherein said yohimbine is yohimbine hydrochloride.

7. The composition for treating impotence in human males as defined in claim 1, wherein said mixture of dried Sturgeon roe and yohimbine is encased in a capsule for oral administration.

8. The composition for treating impotence in human males as defined in claim 7, wherein said capsule contains from about 300 to about 900 mg of said mixture of dried Sturgeon roe and yohimbine.

9. The composition for treating impotence in human males as defined in claim 4, wherein said mixture of dried Sturgeon roe and yohimbine is encased in a capsule for oral administration.

10. The composition for treating impotence in human males as defined in claim 9, wherein said capsule contains from about 300 to about 900 mg of said mixture of dried Sturgeon roe and yohimbine.

11. The composition for treating impotence in human males as defined in claim 10, wherein said capsule contains about 600 mg of said mixture of dried Sturgeon roe and yohimbine.

12. The composition for treating impotence in human males as defined in claim 1, wherein said dried Sturgeon roe is lyophilized roe.

13. The composition for treating impotence in human males as defined in claim 3, wherein said dried Sturgeon roe is lyophilized roe.

14. The composition for treating impotence in human males as defined in claim 10, wherein said dried Sturgeon roe is lyophilized roe.

15. The composition for treating impotence in human males as defined in claim 1, wherein said dried Sturgeon roe is ambient temperature and pressure-dried roe.

16. The composition for treating impotence in human males as defined in claim 3, wherein said dried Sturgeon roe is ambient temperature and pressure-dried roe.

17. The composition for treating impotence in human males as defined in claim 10, wherein said dried Sturgeon roe is ambient temperature and pressure-dried roe.

18. The composition for treating impotence in human males as defined in claim 10, further including a pharmaceutically acceptable preservative.

19. The composition for treating impotence in human males as defined in claim 1, further including one or more supplemental components selected from vitamins, minerals, plant extracts, flavoring agents and coloring agents.

20. A method of treating impotence in human males comprising administration to a male in need of such treatment an effective amount of the composition defined in claim 1.

21. A composition for treating impotence in human males comprising a mixture of dried lyophilized Sturgeon roe and yohimbine, wherein the weight percent ration of said dried roe:yohimbine is from about 25:1 to 1000:1, said roe having a moisture content of at least 30 weight percent, for inclusion in the composition, and prepared by:

a) lyophilizing said roe by exposure to conditions including a temperature of −20° C. or less and a pressure of 300 millitorr or less until the total moisture content of said roe is less than 5 weight percent;

b) grinding said lyophilized roe to a powder; and c) adding to said lyophilized roe powder one or more preservatives selected from methyl paraben, propyl paraben, BHA and BHT.

22. A composition for treating impotence in human males comprising a mixture of dried Sturgeon roe and yohimbine, wherein the weight percent ration of said dried roe:yohimbine is from about 25:1 to 1000:1, said roe having a moisture content under 5 weight percent, for inclusion in the composition, and prepared by:

a) spreading said roe in a thin layer in a tray;

b) placing said tray into a closed environment with temperatures and humidity controls;

c) maintaining said closed environment at about room temperature;

d) periodically mixing and respreading said roe in layers in said tray;

e) circulating air within said closed environment over said roe layers;

f) gradually decreasing the humidity of said closed environment by removing moisture from the air in said environment, until the moisture content of said roe falls below 5 weight percent;

g) removing said roe from said closed environment;

h) grinding said roe to a powder; and i) adding to said roe powder one or more preservatives selected from methyl paraben, propyl paraben, BHA and BHT.

* * * * *